United States Patent
Nemeth et al.

(10) Patent No.: US 6,872,866 B1
(45) Date of Patent: Mar. 29, 2005

(54) LIQUID PHASE PROCESS FOR C8 ALKYLAROMATIC ISOMERIZATION

(75) Inventors: Laszlo T. Nemeth, Barrington, IL (US); Gregory F. Maher, Aurora, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 10/736,312

(22) Filed: Dec. 15, 2003

(51) Int. Cl.$^7$ .............................................. C07C 5/27
(52) U.S. Cl. ....................................................... 585/481
(58) Field of Search ........................................ 585/481

(56) References Cited

U.S. PATENT DOCUMENTS

| | | | |
|---|---|---|---|
| 3,832,449 A | 8/1974 | Rosinski et al. | 423/328 |
| 3,856,871 A | 12/1974 | Haag et al. | 260/668 A |
| 3,856,872 A | 12/1974 | Morrison | 260/668 A |
| 3,970,544 A | 7/1976 | Rosinski et al. | 208/111 |
| 4,152,363 A | 5/1979 | Tabak et al. | 585/481 |
| 4,268,420 A | 5/1981 | Klotz | 252/432 |
| 4,452,769 A | 6/1984 | Chu et al. | 423/329 |
| 4,537,758 A | 8/1985 | Chu et al. | 423/329 |
| 4,891,458 A | 1/1990 | Innes et al. | 585/323 |
| 4,899,011 A | 2/1990 | Chu et al. | 585/481 |
| 4,939,110 A | 7/1990 | Sachtler et al. | 502/66 |
| 4,962,258 A | 10/1990 | Amelse et al. | 585/480 |
| 5,030,786 A | 7/1991 | Shamshoum et al. | 585/467 |
| 5,693,215 A * | 12/1997 | Zones et al. | 208/27 |
| 5,744,673 A | 4/1998 | Skeels et al. | 585/474 |
| 5,750,814 A | 5/1998 | Grootjans et al. | 585/323 |
| 5,763,720 A | 6/1998 | Buchanan et al. | 585/475 |
| 5,789,641 A | 8/1998 | Alario et al. | 585/475 |
| 5,811,612 A | 9/1998 | Girotti et al. | 585/467 |
| 5,942,651 A | 8/1999 | Beech, Jr. et al. | 585/475 |
| 6,222,086 B1 | 4/2001 | Sharma et al. | 585/481 |
| 6,440,886 B1 | 8/2002 | Gajda et al. | 502/64 |
| 6,448,459 B1 | 9/2002 | Magne-Drisch et al. | 585/478 |
| 6,512,155 B1 | 1/2003 | Johnson et al. | 585/481 |
| 6,576,581 B1 | 6/2003 | Sharma et al. | 502/66 |

* cited by examiner

*Primary Examiner*—Thuan D Dang
(74) *Attorney, Agent, or Firm*—John G. Tolomei; James C. Paschall; Thomas K. McBride, Jr.

(57) ABSTRACT

A liquid or partially liquid phase process for isomerizing a non-equilibrium mixture of xylenes and ethylbenzene uses a zeolitic catalyst system preferably based on zeolite beta and on pentasil-type zeolite. The invention obtains an improved yield of para-xylene from the mixture relative to prior art processes in a more economical manner. A preferred beta zeolite is a surface-modified zeolite beta resulting from acid washing of a templated native zeolite at conditions insufficient to effect bulk dealumination. A preferred pentasil zeolite is a MTW-type with a silica-to-alumnina ratio between 20 and 45.

4 Claims, No Drawings

LIQUID PHASE PROCESS FOR C8 ALKYLAROMATIC ISOMERIZATION

FIELD OF THE INVENTION

The present invention relates to catalytic hydrocarbon conversion, and more specifically to the use of a catalyst system comprising pentasil zeolite such as MTW-type zeolite and beta zeolite in aromatics isomerization, and even more specifically to a process without hydrogen addition to convert a non-equilibrium feed depleted in para-xylene into an equilibrium product that is enriched in para-xylene.

BACKGROUND OF THE INVENTION

The xylenes, para-xylene, meta-xylene and ortho-xylene, are important to intermediates that find wide and varied application in chemical syntheses. Para-xylene upon oxidation yields terephthalic acid that is used in the manufacture of synthetic textile fibers and resins. Meta-xylene is used in the manufacture of plasticizers, azo dyes, wood preservers, etc. Ortho-xylene is feedstock for phthalic anhydride production.

Xylene isomers from catalytic reforming or other sources generally do not match demand proportions as chemical intermediates. Further, xylene isomers are generally present with ethylbenzene, which is difficult to separate or to convert. Para-xylene in particular is a major chemical intermediate with rapidly growing demand, but amounts to only 20 to 25% of a typical $C_8$ aromatics stream. Adjustment of isomer ratio to demand can be effected by combining xylene-isomer recovery, such as adsorption for para-xylene recovery, with isomerization to yield an additional quantity of the desired isomer. Isomerization converts a non equilibrium mixture of the xylene isomers that is lean in the desired xylene isomer to a mixture approaching equilibrium concentrations.

Various catalysts and processes have been developed to effect xylene isomerization. In selecting appropriate technology, it is desirable to run the isomerization process as close to equilibrium as practical in order to maximize the para-xylene yield; however, associated with this is a greater cyclic $C_8$ loss due to side reactions. The approach to equilibrium that is used is an optimized compromise between high $C_8$ cyclic loss at high conversion (i.e., very close approach to equilibrium) and high utility costs due to the large recycle rate of unconverted $C_8$ aromatics. Catalysts thus are evaluated on the basis of a favorable balance of activity, selectivity and stability.

Catalysts containing molecular sieves have become prominent for xylene isomerization in the past quarter-century or so. U.S. Pat. No. 3,856,872, for example, teaches xylene isomerization and ethylbenzene conversion with a catalyst containing ZSM-5 (MFI-type), ZSM-12 (MTW-type (IUPAC Commission on Zeolitic Nomenclature)), or ZSM-21 zeolite. U.S. Pat. No. 4,899,011 discloses isomerization of $C_8$ aromatics using two zeolites such as ZSM-5 with different crystal sizes, each of which is associated with a strong hydrogenation metal. U.S. Pat. No. 4,939,110 discloses a catalyst for isomerization using two metals and a pentasil zeolite, which includes ZSM-12 (MTW-type) zeolite. U.S. Pat. No. 6,222,086 and U.S. Pat. No. 6,576,581 disclose a dual catalyst system for aromatics isomerization using at least one non-zeolitic molecular sieve and one zeolitic aluminosilicate. U.S. Pat. No. 6,448,459 discloses a liquid phase isomerization stage and a gas phase isomerization stage with EUO-type zeolite.

U.S. Pat. No. 4,962,258 discloses a process for liquid phase xylene isomerization over gallium-containing, crystalline silicate molecular sieves as an improvement over aluminosilicate zeolites ZSM-5, ZSM-12 (MTW-type), and ZSM-21 as shown in U.S. Pat. No. 3,856,871. The '258 patent refers to borosilicate work, as exemplified in U.S. Pat. No. 4,268,420, and to zeolites of the large pore type such as faujasite or mordenite. U.S. Pat. No. 5,744,673 discloses an isomerization process using beta zeolite and exemplifies the use of gas phase conditions with hydrogen.

U.S. Pat. No. 5,763,720 discloses a gas phase $C_9$ aromatics transalkylation process with a treated MTW-type or alternatively with a treated beta zeolite, both with a hydrogenation metal component; U.S. Pat. No. 5,942,651 further discloses a two zeolite system with the first zeolite from U.S. Pat. No. 5,763,720 combined with a second zeolite with smaller pores such as ZSM-5. A two zeolite catalyst system for transalkylation was also disclosed in U.S. Pat. No. 5,789,641 with a first catalyst of mordenite and a second catalyst of mazzite. Other processes have referred to zeolite beta in the context of ethylbenzene production. U.S. Pat. No. 4,891,458 discloses a process for alkylation or transalkylation of an aromatic hydrocarbon, such as benzene, with an olefin alkylating agent or polyalkyl aromatic hydrocarbon transalkylating agent, under at least partial liquid phase conditions over zeolite beta. U.S. Pat. No. 5,030,786 discloses a dehydration process to reduce the water level for a mono-alkyl-benzene production process based on zeolite beta or zeolite Y. U.S. Pat. No. 5,750,814 teaches that the use of beta in a process for ethylbenzene production, via alkylation, which actually minimizes xylene production (see column 3, line 27). U.S. Pat. No. 5,811,612 discloses that diethylbenzene can be transalkylated with benzene to produce ethylbenzene. U.S. Pat. No. 6,440,886 discloses a surface-modified zeolite beta by treating a templated native zeolite with an acid prior to template-removal calcination.

SUMMARY OF THE INVENTION

Most gas phase processes are capital intensive and require installation of a fired heater, compressor, and gas-liquid separation system. A liquid phase process reduces required equipment to a reactor and heat exchanger thus saving considerable capital. Also, most gas phase processes use hydrogen to promote stability, which can be eliminated in a liquid phase process, thus saving hydrogen consumption and reducing loss of aromatics rings due to hydrogen saturation.

Accordingly, a principal object of the present invention is to provide a liquid phase process for the isomerization of alkylaromatic hydrocarbons. More specifically, the process of the present invention is directed to catalytic isomerization of $C_8$ aromatic hydrocarbons over a beta zeolite and a pentasil zeolite such as MTW-type zeolite in order to obtain improved yields of desired xylene isomers.

Another broad embodiment of the present invention is directed toward a catalyst system for the isomerization of alkylaromatics based upon contacting a $C_8$-aromatics rich hydrocarbon feed stream comprising less than the equilibrium amount of para-xylene with a catalyst comprising beta zeolite and a catalyst comprising a pentasil zeolite such as MT-zeolite. The contacting occurs under at least partial liquid phase conditions in the absence of substantial hydrogen and allows a product stream to be recovered which comprises a greater amount of para-xylene than the feed stream. Preferably the amount of para-xylene in the product stream is at or greater than the equilibrium amount.

These, as well as other objects and embodiments will become evident from the following detailed description of the invention.

DETAILED DESCRIPTION OF THE INVENTION

The feedstocks to the aromatics isomerization process of this invention comprise isomerizable alkylaromatic hydrocarbons of the general formula $C_6H_{(6-n)}R_n$, where n is an integer from 2 to 5 and R is $CH_3$, $C_2H_5$, $C_3H_7$, or $C_4H_9$, in any combination and including all the isomers thereof. Suitable alkylaromatic hydrocarbons include, for example but without so limiting the invention, ortho-xylene, meta-xylene, para-xylene, ethylbenzene, ethyltoluenes, tri-methylbenzenes, di ethylbenzenes, tri-ethylbenzenes, methylpropylbenzenes, ethylpropylbenzenes, di-isopropylbenzenes, and mixtures thereof.

A particularly preferred application of the catalyst system of the present invention is the isomerization of a $C_8$ aromatic mixture containing ethylbenzene and xylenes. Generally the mixture will have an ethylbenzene content of about 1 to about 50 mass-%, an ortho-xylene content of 0 to about 35 mass-%, a meta-xylene content of about 20 to about 95 mass-% and a para-xylene content of 0 to about 30 mass-%. The aforementioned $C_8$ aromatics are a non-equilibrium mixture, i.e., at least one $C_8$ aromatic isomer is present in a concentration that differs substantially from the equilibrium concentration at isomerization conditions. Usually the non-equilibrium mixture is prepared by removal of para-, ortho- and/or meta-xylene from a fresh $C_8$ aromatic mixture obtained from an aromatics-production process.

The alkylaromatic hydrocarbons may be utilized in the present invention as found in appropriate fractions from various refinery petroleum streams, e.g., as individual components or as certain boiling-range fractions obtained by the selective fractionation and distillation of catalytically cracked or reformed hydrocarbons. Concentration of the isomerizable aromatic hydrocarbons is optional; the process of the present invention allows the isomerization of alkylaromatic-containing streams such as catalytic reformate with or without subsequent aromatics extraction to produce specified xylene isomers and particularly to produce para-xylene. A $C_8$ aromatics feed to the present process may contain nonaromatic hydrocarbons, i.e., naphthenes and paraffins, in an amount up to about 30 mass-%. Preferably, the isomerizable hydrocarbons consist essentially of aromatics, to ensure pure products from downstream recovery processes. Moreover, a $C_8$ aromatics feed that is rich in undesired ethylbenzene can be supplied such that it can be converted to xylenes or other non-$C_8$ compounds in order to further concentrate desired xylene species.

According to the process of the present invention, an alkylaromatic hydrocarbon feed mixture, in the absence of a substantial amount of hydrogen, is contacted with two or more catalysts of the type hereinafter described in an alkylaromatic-hydrocarbon isomerization zone. A substantial amount of hydrogen refers to greater than dilute amounts, which may already be present, by being dissolved in the liquid, and further refers to the fact that no hydrogen is added. It is preferred that the absence of a substantial amount of hydrogen be less than or equal to the hydrogen solubility in the liquid phase, which will be less than 1 wt-%. Contacting may be effected using the catalyst system in a fixed-bed system, a moving-bed system, a fluidized-bed system, a slurry system, and an ebullated-bed system or in a batch-type operation. In view of the danger of attrition loss of valuable catalysts and of the simpler operation, it is preferred to use a fixed-bed system. In this system, the feed mixture is preheated by suitable heating means to the desired reaction temperature, such as by heat exchange with another stream if necessary, and then passed into an isomerization zone containing a fixed bed or beds of catalyst(s). The isomerization zone may be one or more separate reactors with suitable means therebetween to ensure that the desired isomerization temperature is maintained at the entrance to each zone. The reactants may be contacted with the catalyst bed in upward-, downward-, or radial-flow fashion, and the reactants may be in the liquid phase or a mixed liquid-vapor phase.

Isomerization catalysts comprising single or multiple combinations of zeolites beta and pentasil type (such as MTW) may be contained in separate reactors, arranged sequentially in the same reactor, mixed physically, or composited as a single catalyst. The use of the term catalyst system is understood to encompass all of these conceptual options. By employing a single reactor, however, savings are realized in piping, instrumentation and other appurtenances. Physical mixing of the catalysts would facilitate synergistic reactions of the catalysts, but separation and recovery of catalyst components would be more difficult. The system of catalysts optionally may be repeated in one or more additional stages, i.e., reactants from the contacting of the feed are processed in another sequence of multiple catalysts.

In an alternative embodiment of the invention, therefore, the reactor contains a physical mixture of individual catalysts containing the beta zeolite and the MTW-type zeolite. In this embodiment, particles are mechanically mixed to provide the catalyst system of the invention. The particles can be thoroughly mixed using known techniques such as mulling to intimately blend the physical mixture. Although the first and second particles may be of similar size and shape, the particles preferably are of different size and/or density for ease of separation for purposes of regeneration or rejuvenation following their use in hydrocarbon processing.

As yet another alternative embodiment of the present invention, a physical mixture of beta zeolite and MTW-type zeolite is contained within the same catalyst particle. In this embodiment, the sieves may be ground or milled together or separately to form particles of suitable size, preferably less than 100 microns, and the particles are supported in a suitable matrix. Optimally, the matrix is selected from an inorganic oxide hereinafter described. As a variant of this embodiment, the zeolites are as a multi-compositional, multi-phase composite having contiguous phases, especially wherein one phase comprises a deposition substrate upon which another phase is deposited as an outer layer.

The alkylaromatic feed mixture, preferably a non-equilibrium mixture of $C_8$ aromatics, is contacted with the isomerization catalysts at suitable alkylaromatic-isomerization conditions. Such conditions comprise a temperature ranging from about 100° to about 400° C. or more, and preferably in the range from about 150° to 300° C. The pressure generally is from about 10 kPa to about 5 MPa absolute, preferably from about 100 kPa to about 3 MPa absolute. A sufficient volume of catalyst comprising the catalyst system is contained in the isomerization zone to provide a liquid hourly space velocity with respect to the hydrocarbon feed mixture of from about 0.1 to 20 $hr^{-1}$, and preferably 0.5 to 10 $hr^{-1}$. If the two or more catalysts are contained in separate beds, different operating conditions within the above constraints may be used within each of the beds in order to achieve optimum overall results.

The particular scheme employed to recover an isomerized product from the effluent of the reactors of the isomerization zone is not deemed to be critical to the instant invention, and any effective recovery scheme known in the art may be used.

Typically, the liquid product is fractionated to remove light and/or heavy byproducts to obtain the isomerized product. Heavy byproducts include $A_{10}$ compounds such as dimethylethylbenzene. In some instances, certain product species such as ortho-xylene or dimethylethylbenzene may be recovered from the isomerized product by selective fractionation. The product from isomerization of $C_8$ aromatics usually is processed to selectively recover the para-xylene isomer, optionally by crystallization. Selective adsorption is preferred using crystalline aluminosilicates according to U.S. Pat. No. 3,201,491. Improvements and alternatives within the preferred adsorption recovery process are described in U.S. Pat. No. 3,626,020, U.S. Pat. No. 3,696,107, U.S. Pat. No. 4,039,599, U.S. Pat. No. 4,184,943, U.S. Pat. No. 4,381,419 and U.S. Pat. No. 4,402,832, incorporated herein by reference.

As noted hereinabove, the present invention is drawn to a catalyst system and its use in isomerization of $C_8$ aromatics comprising a beta zeolite first catalyst and a MTW-type zeolite second catalyst, optionally having various contents of platinum-group metal components. The mass ratio of first catalyst to second catalyst depends primarily on the feedstock composition and desired product distribution, with a first:second catalyst mass ratio of from about 1:50 to about 50:1 being preferred and from about 1:20 to 20:1 being especially preferred. The catalyst system of the invention may include other catalysts, either molecular sieve-based or amorphous. Such other catalysts include but are not limited to zeolite mordenite, zeolite Y, ZSM-5, PSH-3, MCM-22, MCM-36, MCM-49, and MCM-56. Zeolite Y is described in U.S. Pat. No. 3,130,007.

An essential component of the first catalyst of the present invention therefore is at least one zeolite beta molecular sieve. Zeolite beta is described in U.S. Pat. No. 3,308,069 and US Re 28,341. Suitable zeolite betas include, but are not limited to, pristine zeolite beta in which the H+ ion has at least partially replaced the contained metal cation, as disclosed in EP 432,814 B1; and zeolite beta into which certain quantities of alkaline, alkaline-earth, or metallic cations have been introduced by ion exchange, as disclosed in U.S. Pat. No. 5,672,799. Various modifications of zeolite beta are also suitable for use in this invention. Suitable modified zeolite betas include, but are not limited to, zeolite beta which has been modified by steam treatment and ammonium ion treatment, as disclosed in U.S. Pat. No. 5,522,984; and zeolite beta in which the H+ ion has at least partially replaced the contained metal cation, with the zeolite beta being modified by isomorphous substitution of aluminum by boron, gallium, or iron, as disclosed in EP 432,814 B1. Suitable zeolites for use in this invention also include zeolites that are synthesized by modified preparation methods, such as, but not limited to, a preparation method comprising forming a reaction mixture comprising water, a source of silicon dioxide, a source of fluoride ions, a source of tetraethylammonium cations, and, optionally, a source of an oxide of a trivalent element, as disclosed in WO 9733830.

A highly preferred zeolite beta for use in the present invention is disclosed in U.S. Pat. No. 5,723,710, the teachings of which are incorporated herein by reference. This preferred zeolite is a surface-modified zeolite beta which results from acid washing of a templated native zeolite beta. That is, the formation of the surface-modified zeolite beta starts with a templated beta where the template is, for example, a tetraalkylammonium salt, such as tetraethylammonium salt. The templated zeolite beta is acid washed in order to protect the internal sites of the zeolite and to prevent dealumination. The templated zeolite beta is treated with a strong acid at a pH between about 0 up to about 2, although a pH under 1 is preferred. Acids which may be used include nitric acid, sulfuric acid, phosphoric acid, and so forth. For example, a weak, 0.01 molar nitric acid may be used in conjunction with ammonium nitrate to perform the acid wash, although substantially higher concentrations, up to about 20 wt-% nitric acid, are preferred. Nitric acid is a preferred acid since it is a non-complexing acid and therefore does not encourage dealumination. Treatment of the templated zeolite beta with strong acid may be effected over the temperature range between about 20° C. (68° F.) up to about 125° C. (257° F.). It is important that acid washing be done under conditions not so severe as to effect dealumination.

The time over which acid washing is conducted in preparing the preferred zeolite is quite temperature dependent. The formation of the surface-modified zeolite beta should avoid significant bulk dealumination of the zeolite. Thus, as a general statement it can be said that acid washing should be done for a time insufficient to effect dealumination. For example, using 0.01 molar nitric acid and about 40% ammonium nitrate at 70° C. (158° F.), contact times of 2 to 3 hours are found adequate to modify the environment of surface aluminum without causing significant bulk dealumination. Using about 15% nitric acid with ammonium nitrate to treat about 25 wt-% slurry at 85° C. (185° F.), a 90-minute treatment is effective. The dependent variables in acid washing include acid concentration, slurry concentration, time and temperature, and suitable conditions at which surface-modified zeolite beta can be prepared without significant bulk dealumination are readily determined by the skilled artisan.

Next the template is removed by calcination at temperatures in the range of 550° to 700° C. (1022° to 1292° F.). Calcination conditions are well known in the art and need not be elaborated upon here. Therefore, in the more usual case after the templated zeolite beta is acid washed it is mixed with a conventional binder, extruded, and the extrudate is ultimately calcined. But the critical portion of the preparation of the preferred zeolite is the acid wash of the templated beta according to the foregoing description.

The preferred zeolitic aluminosilicates of the second catalyst are selected from those which have a silica-to-alumina (Si:$Al_2$) ratio greater than about 10, preferably greater than 20 and less than about 45, and a pore diameter of about 5 to 8 angstroms (Å). Specific examples of suitable zeolites using IUPAC Commission on Zeolite Nomenclature are the MFI, MEL, EUO, FER, MFS, MTT, MTW, TON, MOR and FAU types of zeolites. Pentasil zeolites MFI, MEL, MTW and TON are preferred, and MTW-type zeolites, often designated ZSM-12, are especially preferred.

The preparation of the preferred MTW-type zeolites by crystallizing a mixture comprising an alumina source, a silica source and templating agent using methods well known in the art. U.S. Pat. No. 3,832,449, which is herein incorporated by reference, more particularly describes an MTW-type zeolite using tetraalkylammonium cations. U.S. Pat. No. 4,452,769 and U.S. Pat. No. 4,537,758, which are incorporated herein by reference, use a methyltriethylammonium cation to prepare a highly siliceous MTW-type zeolite.

The beta zeolite and the MTW-type zeolite each preferably are respectively composited with a binder for convenient formation of catalyst particles, either onto the same particle or separate particles. The proportion of beta zeolite in the first catalyst is about 5 to 90 mass-%, preferably about 10 to 80 mass-%, the remainder other than metal and other components discussed herein being the binder component. The relative proportion of MTW-type zeolite in the second catalyst may range from about 1 to about 99 mass-%, with about 50 to about 90 mass-% being preferred for liquid phase isomerization.

As mentioned previously, a binder will be used for both the first and second catalysts, and thus each catalyst will contain a zeolite that will typically be used in combination with a refractory inorganic oxide binder. The binder should be a porous, adsorptive support having a surface area of about 25 to about 500 m$^2$/g. It is intended to include within the scope of the present invention binder materials which have traditionally been utilized in hydrocarbon conversion catalysts such as: (1) refractory inorganic oxides such as alumina, titania, zirconia, chromia, zinc oxide, magnesia, thoria, boria, silica-alumina, silica-magnesia, chromia-alumina, alumina-boria, silica-zirconia, phosphorus-alumina, etc.; (2) ceramics, porcelain, bauxite; (3) silica or silica gel, silicon carbide, clays and silicates including those synthetically prepared and naturally occurring, which may or may not be acid treated, for example, attapulgite clay, diatomaceous earth, fuller's earth, kaolin, kieselguhr, etc.; (4) crystalline zeolitic aluminosilicates, either naturally occurring or synthetically prepared such as FAU, MEL, MFI, MOR types, in hydrogen form or in a form which has been exchanged with metal cations, (5) spinels such as $MgAl_2O_4$, $FeAl_2O_4$, $ZnAl_2O_4$, $CaAl_2O_4$, and other like compounds having the formula MO $Al_2O_3$ where M is a metal having a valence of 2; and (6) combinations of materials from one or more of these groups.

A preferred refractory inorganic oxide for use in the present invention is alumina. Suitable alumina materials are the crystalline aluminas known as the gamma-, eta-, and theta-alumina, with gamma- or eta-alumina giving the best results.

A form for the catalyst composite is an extrudate. The well-known extrusion method initially involves mixing of the molecular sieve with optionally the binder and a suitable peptizing agent to form a homogeneous dough or thick paste having the correct moisture content to allow for the formation of extrudates with acceptable integrity to withstand direct calcination. Extrudability is determined from an analysis of the moisture content of the dough, with moisture content in the range of from about 30 to about 50 wt-% being preferred. The dough is then extruded through a die pierced with multiple holes and the spaghetti-shaped extrudate is cut to form particles in accordance with techniques well known in the art. A multitude of different extrudate shapes is possible, including, but not limited to, cylinders, cloverleaf, dumbbell and symmetrical and asymmetrical polylobates. It is also within the scope of this invention that the extrudates may be further shaped to any desired form, such as spheres, by marumerization or any other means known in the art.

An alternative form of the composite is a sphere continuously manufactured by the well-known oil drop method. Preparation of alumina-bound spheres generally involves dropping a mixture of molecular sieve, alumina sol, and gelling agent into an oil bath maintained at elevated temperatures. Alternatively, gelation of a silica hydrosol may be effected using the oil-drop method. One method of gelling this mixture involves combining a gelling agent with the mixture and then dispersing the resultant combined mixture into an oil bath or tower which has been heated to elevated temperatures such that gelation occurs with the formation of spheroidal particles. The gelling agents that may be used in this process are hexamethylene tetraamine, urea or mixtures thereof. The gelling agents release ammonia at the elevated temperatures which sets or converts the hydrosol spheres into hydrogel spheres. The spheres are then continuously withdrawn from the oil bath and typically subjected to specific aging treatments in oil and an ammoniacal solution to further improve their physical characteristics.

Preferably the resulting composites are then washed and dried at a relatively low temperature of about 50° to 200° C. and subjected to a calcination procedure at a temperature of about 450° to 700° C. for a period of about 1 to about 20 hours.

The catalysts optimally are subjected to steaming to tailor their acid activity. The steaming may be effected at any stage of the zeolite treatment, but usually is carried out on the composite of zeolite binder prior to incorporation of an optional platinum-group metal. Steaming conditions comprise a water concentration of about 5 to 100 vol-%, pressure of from about 100 kPa to 2 MPa, and temperature of between about 600° and 1200° C.; the steaming temperature preferably between about 650° and 1000° C., more preferably at least about 750° C. and optionally may be about 775° C. or higher. In some cases, temperatures of about 800° to 850° C. or more may be employed. The steaming should be carried out for a period of at least one hour, and periods of 6 to 48 hours are preferred. Alternatively or in addition to the steaming, the composite may be washed with one or more of a solution of ammonium nitrate, a mineral acid, and/or water. The washing may be effected at any stage of the preparation, and two or more stages of washing may be employed. Composites may also be treated with silica or carbon materials by means well known in the art.

Catalysts of the invention may optionally comprise a hydrogenation metal, especially a platinum-group metal, including one or more of platinum, palladium, rhodium, ruthenium osmium, and iridium. But preferably, the catalysts of the invention may be essentially free of any metal hydrogenation components, which are considered unnecessary for liquid phase operation. However, if present then the optional hydrogenation metal is a platinum-group metal, and preferably is plating. The platinum-group metal generally comprises from about 0.1 to about 2 mass-% of the final catalyst calculated on an elemental basis. The platinum-group metal component may exist within the final catalyst composite as a compound such as an oxide, sulfide, halide, oxysulfide, etc., or as an elemental metal or in combination with one or more other ingredients of the catalyst composite. It is believed that the best results are obtained when substantially all the platinum-group metal component exists in a reduced state.

The optional platinum-group metal component may be incorporated into the catalyst composite in any suitable manner. One method of preparing the catalyst involves the utilization of a water-soluble, decomposable compound of a platinum-group metal to impregnate the calcined sieve/binder composite. Alternatively, a platinum-group metal compound may be added at the time of compositing the sieve component and binder. Complexes of platinum group metals which may be employed in impregnating solutions, co-extruded with the sieve and binder, or added by other known methods include chloroplatinic acid, chloropalladic acid, ammonium chloroplatinate, bromoplatinic acid, platinum trichloride, platinum tetrachloride hydrate, platinum dichlorocarbonyl dichloride, tetramine platinic chloride, dinitrodiaminoplatinum, sodium tetranitroplatinate (II), palladium chloride, palladium nitrate, palladium sulfate, diaminepalladium (II) hydroxide, tetraminepalladium (II) chloride, and the like. It is within the scope of the present invention that the catalyst composites may contain other metal components. Such metal modifiers may include rhenium, tin, germanium, lead, cobalt, nickel, indium, gallium, zinc, uranium, dysprosium, thallium, and mixtures thereof. Catalytically effective amounts of such metal modifiers may be incorporated into the catalysts by any means known in the art to effect a homogeneous or stratified distribution.

The catalysts of the present invention may contain a halogen component, comprising fluorine, chlorine, bromine or iodine or mixtures thereof, with chlorine being preferred. Preferably, however, the catalyst contains no added halogen other than that associated with other catalyst components.

The catalyst composites are dried at a temperature of from about 100° to about 320° C. for a period of from about 2 to about 24 or more hours and, usually, calcined at a temperature of from about 400° to about 650° C. in an air atmosphere for a period of from about 0.1 to about 10 hours until the metallic compounds present are converted substantially to the oxide form. If desired, the optional halogen component may be adjusted by including a halogen or halogen-containing compound in the air atmosphere.

The resultant calcined composites optimally are subjected to a substantially water-free reduction step to ensure a uniform and finely divided dispersion of the optional metallic components. The reduction optionally may be effected in the process equipment of the present invention. Substantially pure and dry hydrogen (i.e., less than 20 vol. ppm $H_2O$) preferably is used as the reducing agent in this step. The reducing agent contacts the catalyst at conditions, including a temperature of from about 200° to about 650° C. and for a period of from about 0.5 to about 10 hours, effective to reduce substantially all of the Group VIII metal component to the metallic state. In some cases the resulting reduced catalyst composite may also be beneficially subjected to presulfiding by a method known in the art to incorporate in the catalyst composite from about 0.05 to about 1.0 mass-% sulfur calculated on an elemental basis.

EXAMPLES

The following examples are presented only to illustrate certain specific embodiments of the invention, and should not be construed to limit the scope of the invention as set forth in the claims. There are many possible other variations, as those of ordinary skill in the art will recognize, within the spirit of the invention.

Example I

Samples of the three catalysts comprising zeolites were prepared for comparative pilot-plant testing.

Catalyst A contained zeolite mordenite bound by alumina prepared in accordance with the teachings of U.S. Pat. No. 4,861,935. As received, mordenite powder was mixed with alumina powder to an approximate weight ratio of 9:1, peptized, extruded, and acid washed by means known in the art.

Catalyst B contained aluminum-phosphate-bound MFI type zeolite prepared in accordance with U.S. Pat. No. 6,143,941. A first solution was prepared by adding phosphoric acid to an aqueous solution of hexamethylenetetraamine (HMT) in an amount to yield a phosphorus content of the finished catalyst equal to about 11 mass-%. A second solution was prepared by adding an ammonia-exchanged MFI-type zeolite having an $Si/Al_2$ ratio of about 39 to enough alumina sol, prepared by digesting metallic aluminum in hydrochloric acid, to yield a zeolite content in the finished catalyst equal to about 67 mass-%. These two solutions were commingled to achieve a homogeneous admixture of HMT, phosphorus, alumina sol, and zeolite. This admixture was dispersed as droplets into an oil bath maintained at about 93° C. The droplets remained in the oil bath until they set and formed hydrogel spheres having a diameter of about 1.6 mm. The spheres were removed from the oil bath, water washed, air dried, and calcined at a temperature of about 550° C. Then the calcined spheres were subjected to steaming at a temperature of about 660° C. in an atmosphere of 40% steam in air. The steamed spheres were then metal-impregnated using a solution of tetraamine platinum chloride. Upon completion of the impregnation, the catalyst was dried, oxidized, and reduced to yield a catalyst containing about 0.04 mass-% platinum.

Catalyst C contained zeolite beta prepared in accordance with U.S. Pat. No. 5,723,710. Commercial zeolite beta chemically comprising $SiO_2$ 92.2 wt-% and $Al_2O_3$ 7.0 wt-%, with a LOI of 24.3 wt-%, and a surface area by $N_2$ BET of 672 $m^2/g$, was obtained. To a solution of 1428 grams ammonium nitrate in 3224 grams distilled water was added 932 grams of 70 wt-% nitric acid and the mixture was heated to 85° C. The zeolite beta (1416 grams dry weight) was added and this mixture was stirred at 85° C. for 90 minutes. The slurry was filtered and washed using 10 liters of distilled water and then dried at 100° C. for 16 hours. Then the zeolite was calcined in air at 650° C. for 3 hours.

Catalyst D contained MTW-type zeolite prepared in accordance with U.S. Pat. No. 4,452,769. To a solution of 0.4 grams sodium hydroxide in 9 grams distilled water was added 0.078 g aluminum hydroxide hydrate and stirred until dissolved. A second solution of 1.96 grams of methyltriethylammonium halide (MTEA-Cl, note here the chloride form was used instead of the bromide form) in 9 grams distilled water was prepared and stirred until dissolved. Then, both solutions were stirred together until homogenized. Next, 3 grams of precipitated silica was added, stirred for 1 hour at room temperature and sealed in a Teflon-lined autoclave for 8 days at 150° C. Zeolite type MTW was recovered after cooling, filtering, and washing with distilled water. After drying a product of 5 $Na_2O:1.25Al_2O_3:50SiO_2:1000H_2O:10(MTEA-Cl)$ with a $N_2$ BET 454 $m^2/g$, was obtained. To form catalyst D, the dry MTW-zeolite powder was calcined and then compressed to form pellets.

Example II

The catalysts were evaluated for liquid phase isomerization of $C_8$ aromatics using a pilot-plant flow reactor processing a non-equilibrium $C_8$ aromatic feed having the following composition in wt-%:

| | |
|---|---|
| Ethylbenzene | 7.17 |
| Para-xylene | 0.03 |
| Meta-xylene | 70.46 |
| Ortho-xylene | 22.28 |
| $C_9^+$ Aromatics | 0.05 |
| $C_9^+$ Non-aromatics | 0.01 |

This feed was contacted with catalyst at a liquid hourly space velocity of about 1.5 $hr^{-1}$. Pressure was at 1200 kPa sufficient to maintain liquid phase. Reactor temperature was adjusted to effect a favorable conversion level. Catalyst C appeared as the most stable catalyst during this testing.

Results were as follows:

| Catalyst | A | B | C |
|---|---|---|---|
| Temperature, ° C. | 247 | 245 | 246 |
| EB conversion, mol-% | 19.7 | 2.1 | 50.1 |
| $C_{10}$ Aromatics | 1.31 | 0.15 | 3.44 |
| p-xylene/xylenes, mol-% | 23.7 | 22.1 | 22.7 |

Catalyst C was particularly effective in converting undesired ethylbenzene isomers while still achieving a good proportion of para-xylene isomers in total xylene isomers.

Example III

A second series of catalytic tests was performed for liquid phase isomerization of $C_8$ aromatics using a pilot-plant flow reactor processing a non-equilibrium $C_8$ aromatic feed having the following composition in wt-%:

| | |
|---|---|
| Ethylbenzene | 10.8 |
| Meta-xylene | 63.6 |
| Ortho-xylene | 25.4 |
| $C_9^+$ | 0.2 |

This feed was contacted with catalyst under constant temperatures with an adjusted weight hourly space velocity (WHSV). Pressure was about 1380 kPa. Results were as follows:

| Catalyst | C | D | (C & D) |
|---|---|---|---|
| Temperature ° C. | 245 | 245 | 240 |
| EB conversion, mol-% | 35.1 | 2.2 | 37 |
| p-xylene/xylenes, mol-% | 20.1 | 22.3 | 22.5 |
| % approach to pX/X equilibrium | 82.6 | 91.7 | 92.5 |
| WHSV, $hr^{-1}$ | 1.3 | 0.5 | 0.4 |

The catalyst system of the present invention combined C and D in a ratio with 50 volume-% of catalyst C to 50 volume-% of catalyst D. The combination catalyst system was loaded in separate sequential reactors, and was particularly effective in converting undesired ethylbenzene isomers while still achieving a superior approach to equilibrium para-xylene as part of total xylenes. Very nearly the same ethylbenzene conversion can be accomplished with the catalyst system combination as can be accomplished with catalyst C alone. Very nearly the same approach to para-xylene equilibrium can be accomplished with the catalyst system combination as with catalyst D alone. Note that the "% approach to pX/X equilibrium" is defined as percentage of the product mixture relative to a calculated equilibrium amount of para-xylene under conditions of room temperature and a pressure of 200 kPa, with a number greater than 90% being considered at least near the equilibrium amount.

What is claimed is:

1. A process for the isomerization of xylenes comprising contacting a $C_8$ aromatics containing hydrocarbon feed steam, which comprises ethylbenzene, with a catalyst system comprising a beta zeolite catalyst and MTW-zeolite catalyst under at least partially liquid phase at isomerization conditions and in the absence of a substantial amount of hydrogen, and recovering a product stream comprising para-xylene, wherein the amount of para-xylene in the product is at least 90 mol-% of the approach to an equilibrium amount of para-xylene to total xylenes and wherein the conversion of ethylbenzene over the catalyst system is at least 20 mol-%.

2. The process of claim 1, wherein the binder is selected from the group consisting of alumina, silica, zeolites, and mixtures thereof.

3. The process of claim 1, wherein the beta zeolite catalyst is essentially free of a metal hydrogenation component by containing less than 0.1 mass-% amount of said metal.

4. The process of claim 1, wherein the isomerization conditions comprise a space velocity from about 0.5 to about 10 $hr^{-1}$, a temperature from about 150° to about 300° C. and a pressure from about 100 kPa to about 3 MPa absolute.

* * * * *